United States Patent [19]

Nishino et al.

[11] Patent Number: 5,297,988
[45] Date of Patent: Mar. 29, 1994

[54] FRAGRANCE SUPPLYING APPARATUS FOR VEHICLE

[75] Inventors: Tomohide Nishino; Toshiaki Fukuta; Yukiya Sassa, all of Nagoya; Kunio Okamoto, Okazaki; Hajime Akado, Anjo, all of Japan

[73] Assignee: Nippondenso Co., Ltd., Kariya, Japan

[21] Appl. No.: 971,614

[22] Filed: Nov. 5, 1992

Related U.S. Application Data

[63] Continuation-in-part of Ser. No. 786,774, Nov. 1, 1991, abandoned.

[30] Foreign Application Priority Data

| Nov. 2, 1990 | [JP] | Japan | 2-298105 |
| Jan. 18, 1991 | [JP] | Japan | 3-4689 |
| Nov. 6, 1991 | [JP] | Japan | 3-318516 |
| Sep. 29, 1992 | [JP] | Japan | 4-283856 |

[51] Int. Cl.$^5$ .............................. B60H 3/00
[52] U.S. Cl. ................... 454/75; 222/644; 422/124; 454/157
[58] Field of Search .............. 222/644, 645, 646; 454/75, 157, 337; 422/124

[56] References Cited

U.S. PATENT DOCUMENTS

| 3,576,593 | 4/1971 | Cicirello | 454/124 X |
| 3,647,116 | 3/1972 | Nixon, Jr. et al. | 222/70 |
| 3,677,441 | 7/1972 | Nixon, Jr. et al. | 222/63 |
| 4,159,672 | 7/1979 | Garquilo et al. | 454/337 |
| 4,677,902 | 7/1987 | Takemasa | 454/157 X |
| 4,867,045 | 9/1989 | Freedman | 454/157 |
| 4,913,034 | 4/1990 | Ripple et al. | 454/157 |
| 5,078,046 | 1/1992 | Mascolo et al. | 454/157 |

FOREIGN PATENT DOCUMENTS

| 0325468 | 7/1989 | European Pat. Off. | 422/124 |
| 9003654 | 6/1990 | Fed. Rep. of Germany . | |
| 2448930 | 9/1980 | France | 422/124 |
| 4735442 | 5/1975 | Japan . | |
| 55-8734 | 1/1980 | Japan . | |
| 58-36557 | 3/1983 | Japan . | |
| 1-75435 | 5/1989 | Japan . | |
| 2-60821 | 3/1990 | Japan . | |
| 2-225125 | 9/1990 | Japan . | |

OTHER PUBLICATIONS

Journal of Nippondenso Technical Disclosure, 67-001, Sep. 15, 1989, p. 1.

Primary Examiner—Harold Joyce
Attorney, Agent, or Firm—Cushman, Darby & Cushman

[57] ABSTRACT

A fragrance supplying apparatus for a vehicle for supplying an interior of an air-conditioning duct of the vehicle with a fragrance or deodrant so that the fragrance or deodrant is carried by a flow of air from a blower of the air-conditioning system into the cabin of the vehicle, the fragrance supplying apparatus including a fragrance supplying apparatus having control valves for controlling the supply of the fragrance or deodrant into the air-conditioning duct; a random number producing unit for producing random numbers; and a control unit for controlling the control valves of the fragrance supplying unit based on the random numbers to set varying patterns of supply and cessation of the fragrance or deodrant.

30 Claims, 15 Drawing Sheets

FRAGRANCE SUPPLYING APPARATUS FOR VEHICLE

CROSS REFERENCE TO RELATED APPLICATION

This application is a continuation-in-part application of Ser. No. 07/786,774 filed on Nov. 1, 1991 abandoned.

BACKGROUND OF THE INVENTION

1. Field of the Invention

The present invention relates to a fragrance supplying apparatus for a vehicle, more particularly to a fragrance supplying apparatus for a vehicle which maintains a pleasant cabin atmosphere over a long period.

2. Description of the Related Art

In the summer and the winter, when car windows are closed and the air-conditioning system is used to cool or heat the cabin interior, there is a problem in that the body sweat of the driver and passengers and cigarette smoke slowly accumulate in the cabin or air-conditioning duct and the machinery and equipment in the air-conditioning system. As a result, it is common to provide an apparatus in the cabin or system so as to eliminate or mask the odor.

Fragrance supplying apparatuses for vehicles which eliminate unpleasant odors and emit pleasant fragrances are commercially available, but it is difficult to maintain a pleasant cabin atmosphere over a long period. For example, such fragrance supplying apparatuses initially release large amounts of the deodorant or fragrance and gradually release less and less along with the passage of time. Also, since the deodorant or fragrance is emitted continuously after the apparatuses are opened, the driver and passengers eventually become physically "acclimated" to it and it loses effect. To solve these problems, Japanese Unexamined Utility Model Publication (Kokai) No. 1-75435, for example, proposes a fragrance supplying apparatus with a lid which opens and closes to supply a fragrance in a vehicle intermittently.

Also, in many cases, the fragrance supplying apparatus is manufactured separate from the air-conditioning system and installed in the system only as a later option. This sometimes requires major modification of the system.

Further, more advanced fragrance supplying apparatuses are activated along with the turning of the ignition switch. In recent systems, however, the blower is not started until various sensors are started and warmed up, so much of the deodorant or fragrance is wasted.

SUMMARY OF THE INVENTION

An object of the present invention is to solve the above-mentioned problems and to provide a fragrance supplying apparatus which keeps the cabin air fresh and pleasant over a long period, is easy to installed, and does not waste the fragrance.

The present invention provides a fragrance supplying apparatus for a vehicle for supplying an interior of an air-conditioning duct of the vehicle with a fragrance supplying apparatus so that the fragrance is carried by a flow of air from a blower of the air-conditioning system into the cabin of the vehicle, the fragrance supplying apparatus including a fragrance supplying apparatus having control valves for controlling the supply of the fragrance into the air-conditioning duct; a random number producing unit for producing random numbers; and a control unit for controlling the control valves of the fragrance supplying apparatus based on the random numbers to set varying patterns of supply and cessation of the fragrance.

With the above construction of the fragrance supplying apparatus, since the fragrance supplying apparatus is operated intermittently by the control unit, a pleasant cabin atmosphere can be maintained at all times under different driving states.

BRIEF DESCRIPTION OF THE DRAWINGS

The objects and features of the present invention will become more apparent from the following description of the preferred embodiments with reference to the accompanying figures, in which.

DESCRIPTION OF THE PREFERRED EMBODIMENTS

Figure 1:
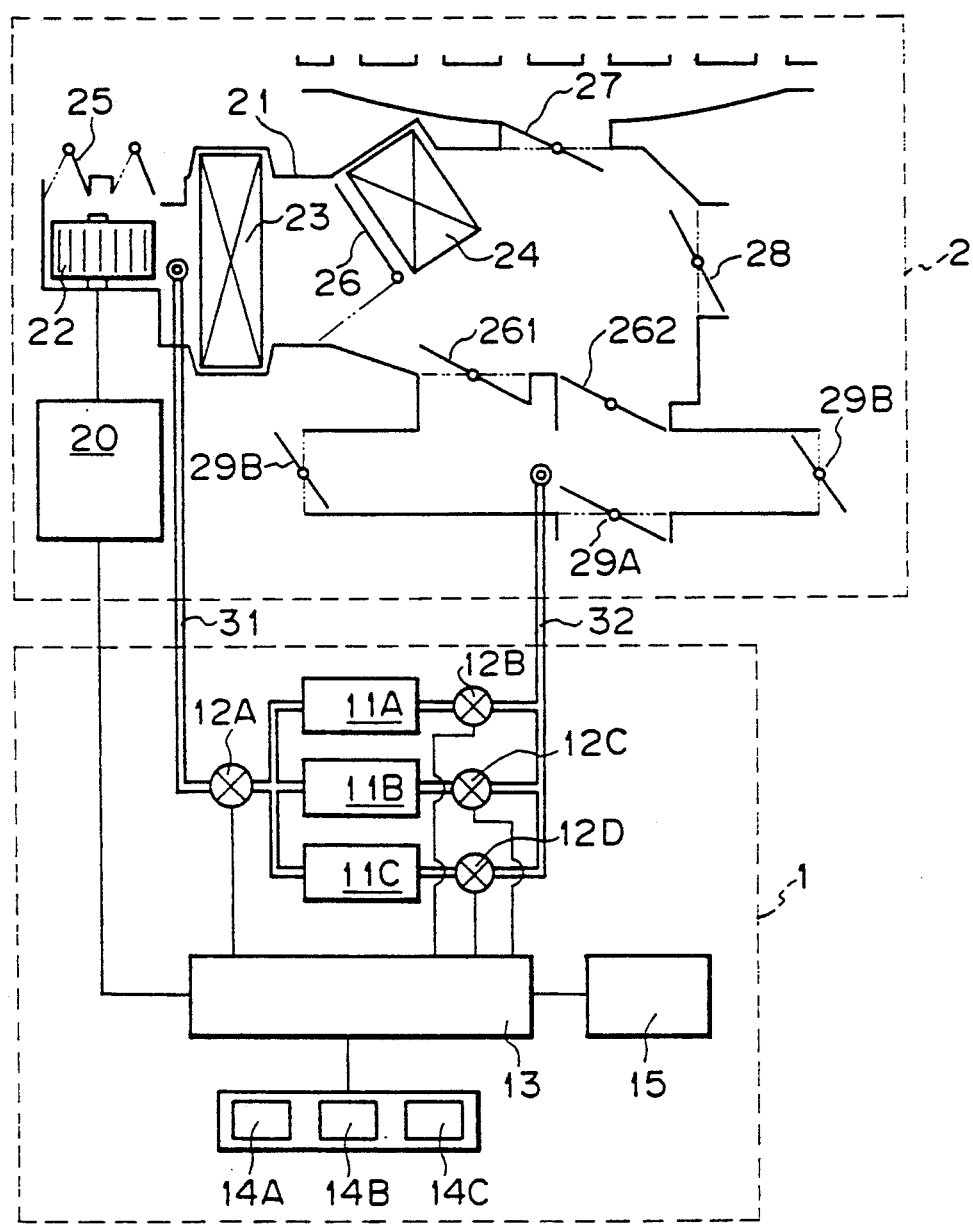
FIG. 1 is a block diagram of the construction of an fragrance supplying apparatus in an air-conditioning system according to a first embodiment of the present invention.

FIG. 1 is a block diagram of the construction of a fragrance supplying apparatus for a vehicle according to a first embodiment of the present invention. Referring to FIG. 1, there is shown an air-conditioning unit 2 having an air-conditioning duct 21 in which there are, from the upstream side, a blower 22, an evaporator 23, and a heater core 24. A switching damper 25 for outside aid inside air, an air mixing damper 26, a maximum cooling damper 261, a mode switching damper 262, etc.

to switch the flow of air therein. A defroster 27, a leg outlet 28, a center register 29A, side register 29B, etc. blow and supply conditioned air. In addition, the above blower 22 is driven by an air-conditioning control circuit 20.

When the blower 22 is operating, inside or outside air is selected by the switching damper 25 is taken into the air-conditioning duct 21 and supplied to the evaporator 23. Some of the cooled and dehumidified air passes through the heater core 24 to be heated and then is mixed downstream by the opening of the mixing damper 26 to become a predetermined temperature of conditioned air.

The conditioned air is supplied to the interior of the cabin when the outlets are selected by the maximum cooling damper 261 and mode switching damper 262.

The fragrance supplying apparatus 1 includes cassettes 11A, 11B, and 11C holding three kinds of fragrances, for example, volatile fragrances. Upstream pipes 31 of these cassettes converge and open at a position upstream of the evaporator 23 through a solenoid valve 12A. Also, downstream pipes 32 of the cassettes 11A to 11C are provided with solenoid valves 12B, 12C, and 12D. These converge downstream and open in the duct 21 near the registers 29A and 29B.

The solenoid valves 12A to 12D are opened and closed by a valve control circuit 13. The valve control circuit 13 is connected at its input to selecting switches 14A, 14B, and 14C for selecting a kind of fragrance and a random number producing circuit 15 for producing 1/f random numbers. The random number producing circuit 15 produces 1/f random numbers where the power spectra are inversely proportional to a frequency f.

In a fragrance supplying apparatus with such a construction, the valve control circuit 13 causes the solenoid valves 11A to 11C for the fragrance cassettes selected by the selecting switches 14A to 14C and the upstream solenoid valve 12A to operate intermittently according to the random numbers from the random number producing circuit 15. Accordingly, air is intermittently introduced through the upstream pipes 31 into the desired fragrance cassettes and volatile fragrances, for example, are intermittently sent into the duct 21 through the downstream pipes 32.

Figure 2:
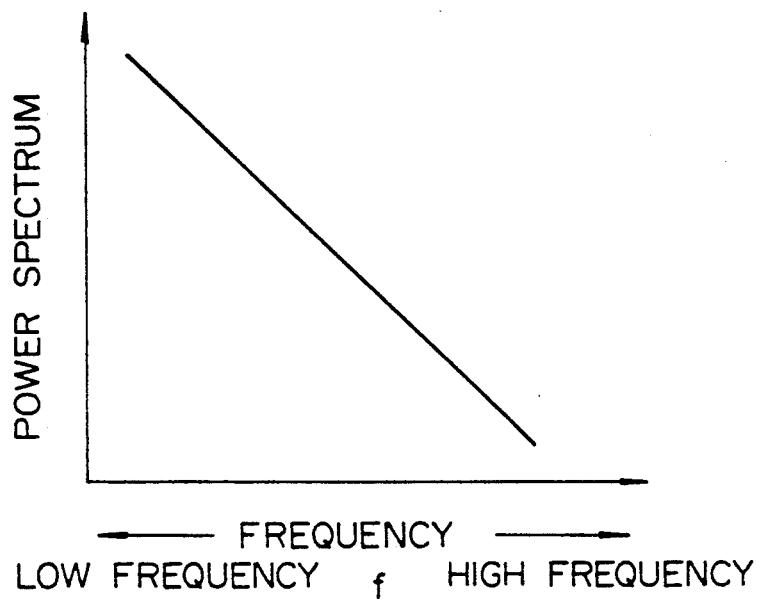
FIG. 2 is a graph of the power spectrum in relation to the frequency in the case of 1/f random numbers.

According to experiments of the inventors, the supply of air may be made 0.3 liter/min to 2.6 liter/min and the diameters of the upstream and downstream pipes are determined to maintain the amount of air. In addition, the time during which a fragrance is supplied may be 3.3 seconds to 9.5 seconds and the interval between when the fragrance is supplied may be 3 minutes to 10 minutes. Different patterns of supplying times and supplying intervals are set and given correspondence to each other, for example a 3.5 second supplying time being paired with a 3 minute supplying interval and a 9.5 second supplying time being paired with a 10 minute supplying interval. Since the frequency f of the different patterns is set, the random number producing circuit 15 produces random numbers designating the above patterns so that the power spectra of the patterns satisfy the relationship of 1/f shown in FIG. 2.

Figure 3:
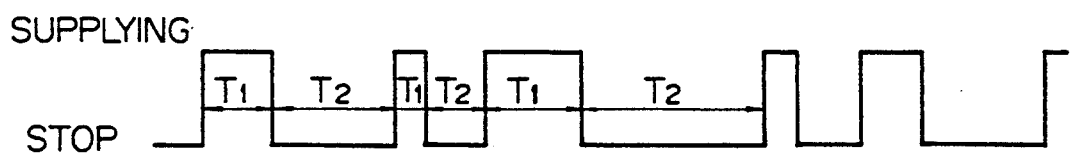
FIG. 3 is a time chart of the operation showing the start and stopping of the supply of a fragrance.

Thus, the valve control circuit 13 intermittently supplies a fragrance into the air-conditioning duct 21 at the supplying time T1 (FIG. 3) and the supplying interval T2 of each pattern designated by the random number output of the random number producing circuit 15.

Figure 5:
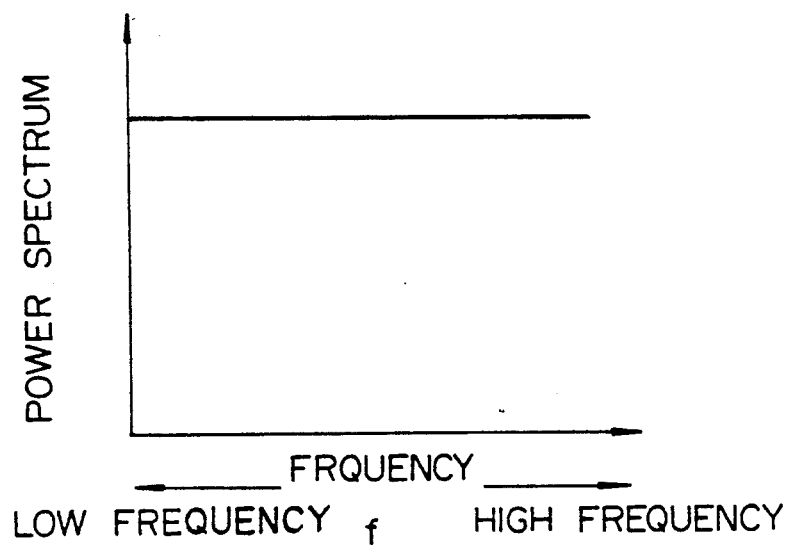
FIG. 5 is a graph of the power spectrum in relation to the frequency in the case of white random numbers.
Figure 6:
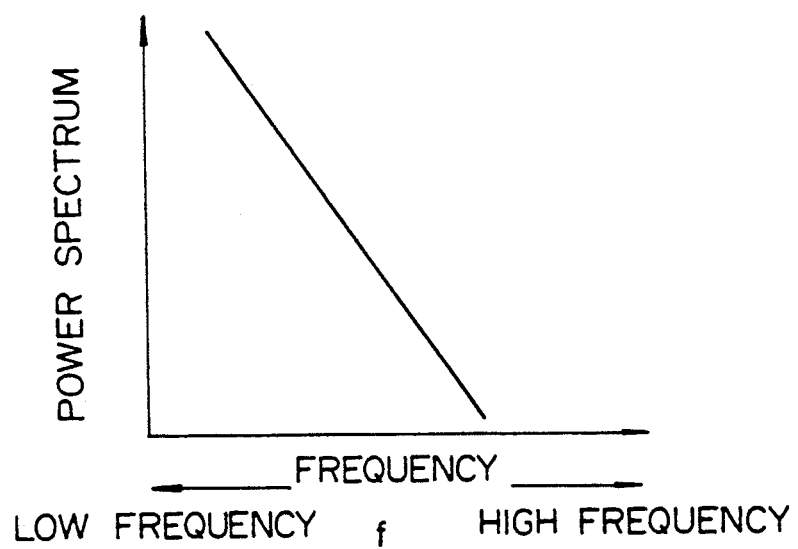
FIG. 6 is a graph of the power spectrum in relation to the frequency in the case of 1/f2 random numbers.

Other random numbers are white random numbers where the power spectra are constant at different frequencies (FIG. 5) and $1/f^2$ random numbers where the power spectra are inversely proportional to the squares of the frequencies (FIG. 6, in which figure the vertical axis is a logarithmic scale). The supply of a fragrance based on the former random numbers seems to be abrupt to the passengers since there is no correlation at all between the period when fragrance is supplied at any one time and the period when it was supplied directly before. On the other hand, the supply of a fragrance based on the latter random numbers has too strong a correlation, so passengers tend to become "acclimated" to the fragrance's effect and feel a lack of freshness.

Compared with these, the supply of a fragrance based on 1/f random numbers (referred to as "1/f fluctuation" hereinafter) is timely and moderate and provides a comfortable stimulus to the passengers.

Figure 4:
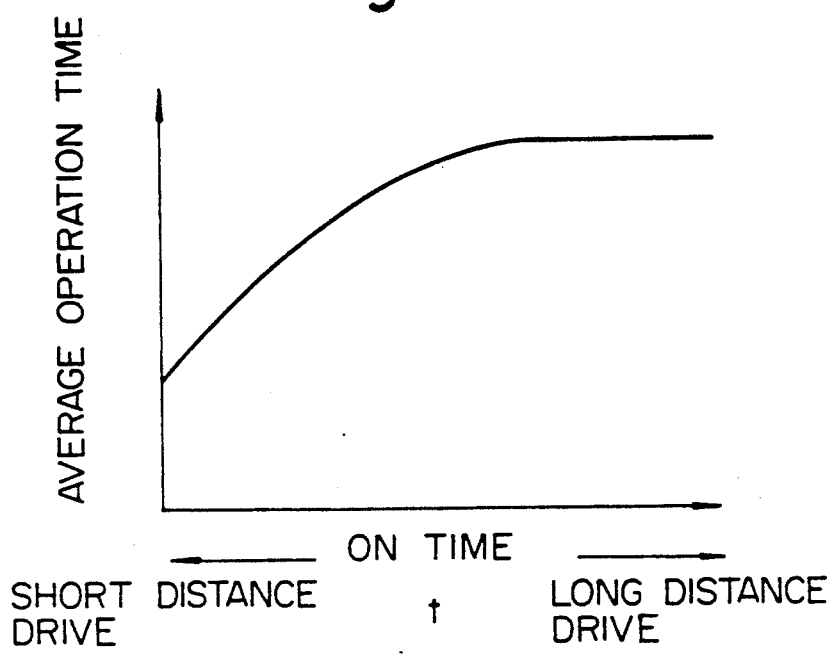
FIG. 4 is a graph of the change of the average operating time over time.

When driving for a relatively short distance, due in part to the fact that the fragrance is supplied only a few times by the above 1/f fluctuation control, the comfort made possible by the above fluctuation control cannot be appreciated. Therefore, as shown in FIG. 4, the valve control circuit 13 supplies the fragrance more frequently for shorter average operating times for a short while after starting the vehicle. As the distance of travel becomes longer, the supply time and interval of the fragrance are returned to normal.

To shorten the average operating time, for example, the supplying times and supplying intervals of the different patterns designated by the random numbers are multiplied by a coefficient of less than 1 which increases along with the travel time.

The average operating time of the intermittent supply of fragrance may be changed not only in accordance with the travel time of the vehicle as mentioned above, but also by the method of determining the degree of fatigue from the R—R interval of the pulse rates of the driver or passengers and shortening the average time when the degree of fatigue is high or the method of shortening the average time when the amount of air from the blower of the air-conditioning apparatus is large.

As set forth above, according to the above embodiment of the present invention, it is possible to consistently obtain a fresh, comfortable cabin atmosphere without abrupt changes in various operating states of the vehicle.

Figure 7:
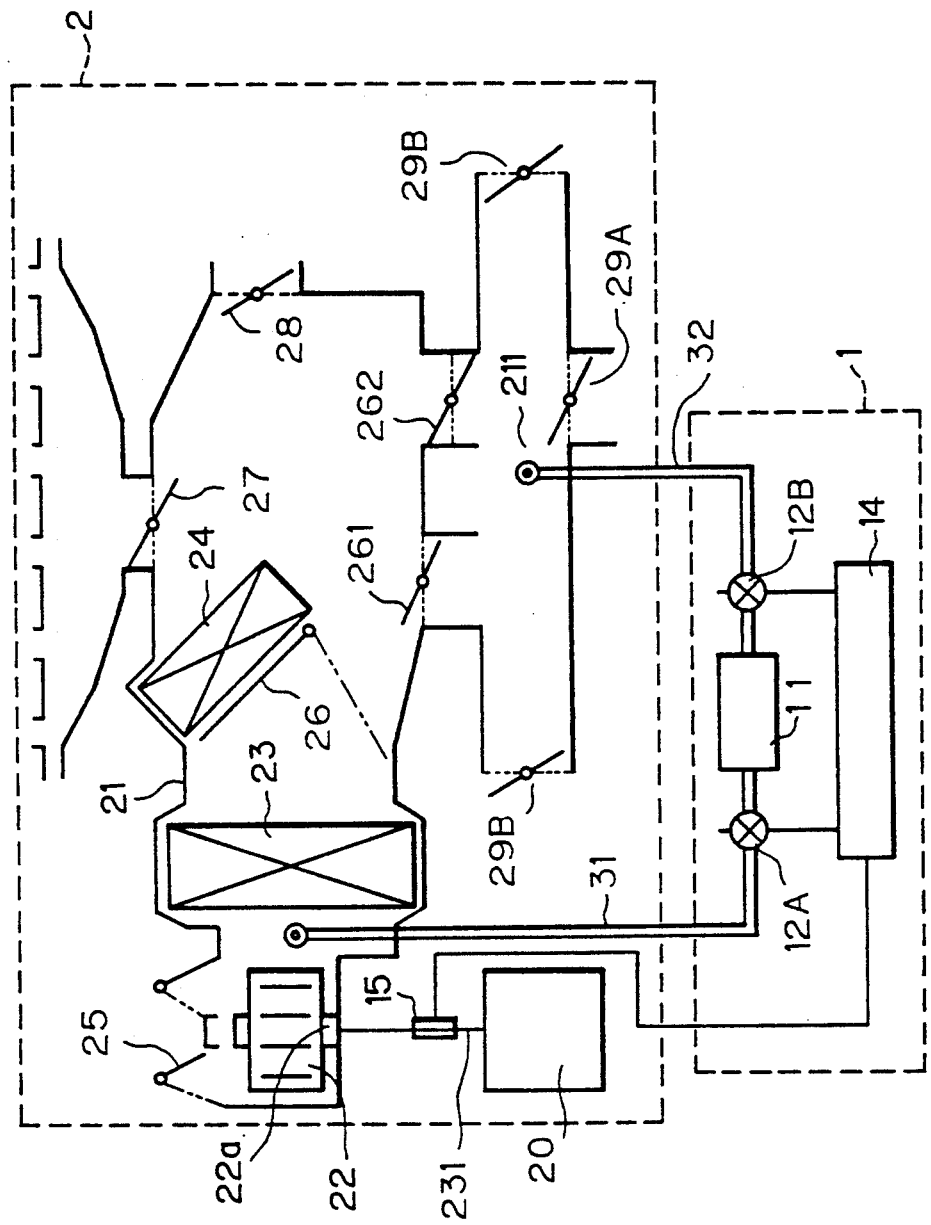
FIG. 7 is a block diagram of the construction of a fragrance supplying apparatus in an air-conditioning system according to a second embodiment of the present invention.

FIG. 7 is a block diagram of the construction of a fragrance supplying apparatus according to a second embodiment of the present invention. As the figure shows, the basic construction is the same as in the first embodiment of the invention shown in FIG. 1. The motor 22a for driving the blower 22 is connected to the air-conditioning control circuit 20 by a feeder 231 to obtain power. The air-conditioning control circuit 20 controls the speed of the blower 22 based on signals of sensors inside and outside the cabin. The feeder 231 is provided with a current sensor 15.

Figure 8:
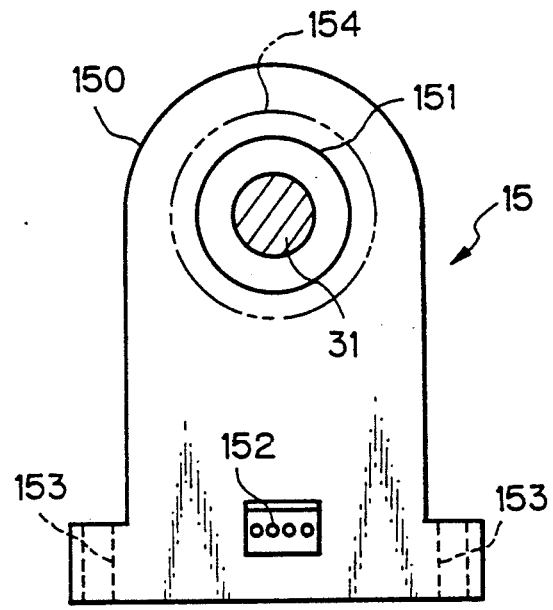
FIG. 8 is a front view of a current sensor.
Figure 9:
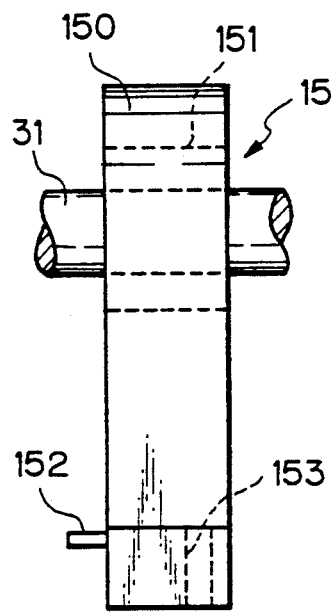
FIG. 9 is a side view of the current sensor.

FIG. 8 is a front view of the current sensor 15, and FIG. 9 is a side view of the sensor. The current sensor 15 shown is that of a sensor using electromagnetic induction, but use may also be made of a Hall element. In FIGS. 8 and 9, the sensor body 150 is made of plastic and has a circular aperture 151 at a semicircular upper half portion into which the feeder 31 is introduced. A detection coil 154 is wound inside the aperture 151. When current flows in the feeder 31, a magnetic field is caused and and electromotive force arises in the detection coil 154.

The sensor body 150 is fixed to a panel of the vehicle surrounding the blower 22 inside the cabin by mounting holes 153 at the two sides Of the lower end. The output of the detection coil 154 is obtained by a connector 152 at the center of the lower end of the body.

Figure 10:
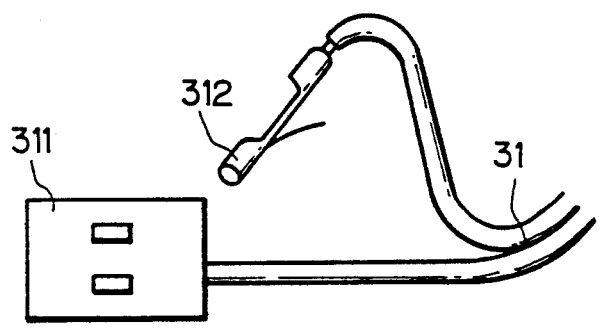
FIG. 10 and FIG. 11 are views of a terminator of a feeder.
Figure 11:
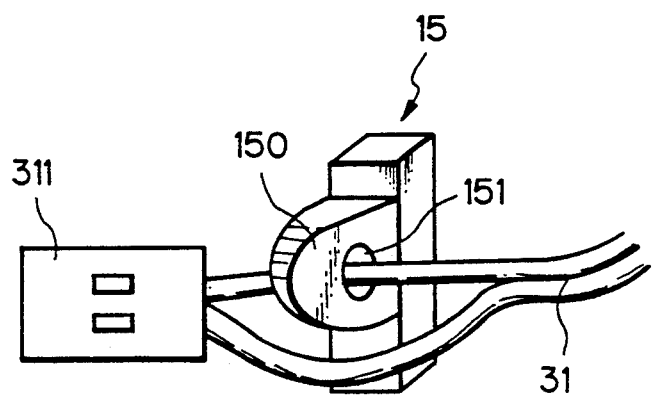

FIGS. 10 to 11 are views of a terminator of the feeder. This facilitates the attachment of the current sensor 15 to the feeder 31. This is, the plus side terminal 312 is pulled out from a feeder connector 311, connected to the blower 22 inside the instrument panel, as shown in FIG. 10. The plus side terminal 312 is then introduced through the aperture 151 of the current sensor 15 and is reinserted into the feeder connector 311, as shown in FIG. 11.

Turning to the operation of this embodiment of the invention, in summary, in the case of a single fragrance cassette, when the blower 22 is powered and thus starts to blow air, the current sensor 15 detects the current and sends out an output signal. The valve control circuit 14 receiving the signal opens the solenoid valves 12A and 12B so as to introduce the air from the blower 22 to the Cassette 11 through the inlet pipe 31. The fragrance is therefore carried by the stream of air and introduced to the three-way branch portion 211 through the outlet pipe 32. In this way, the odors in the air-conditioning system are removed or masked before blowing out of the outlets toward the driver and passengers.

Figure 12:
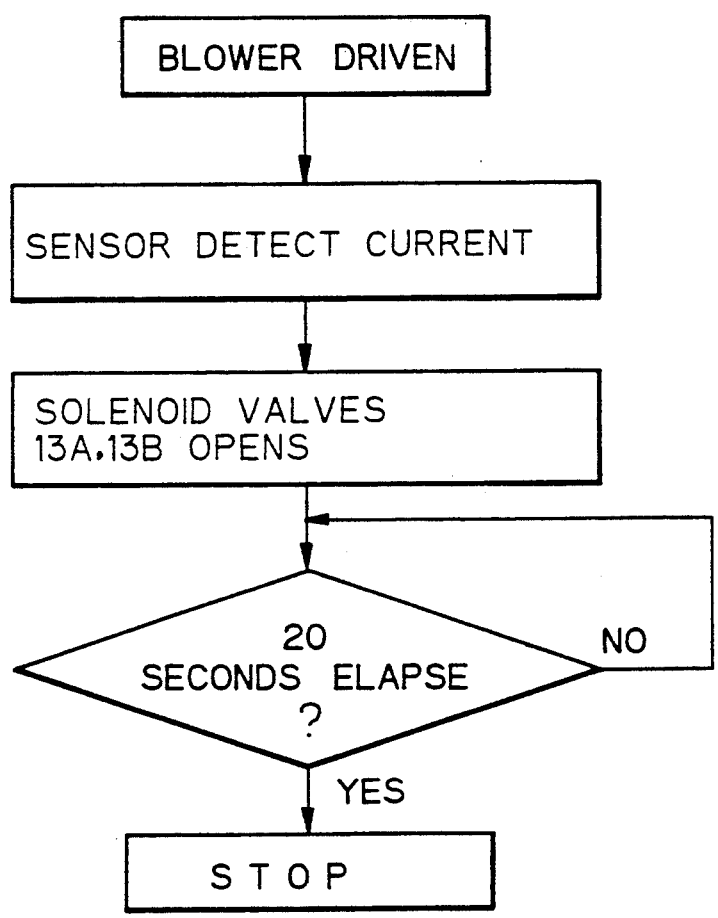
FIG. 12 is a flow chart of the control of a valve control circuit in the case of use of a deodorant.

FIG. 12 is a flow chart of the operation of the valve control circuit in the case of use of a deodorant. When the blower starts to be operated, the current sensor detects the current and the solenoid valves 12A and 12B are opened for a predetermined time, for example 20 seconds after the start of the blower. This enables the odor produced immediately after the startup of the air-conditioning system to be removed.

Figure 13:
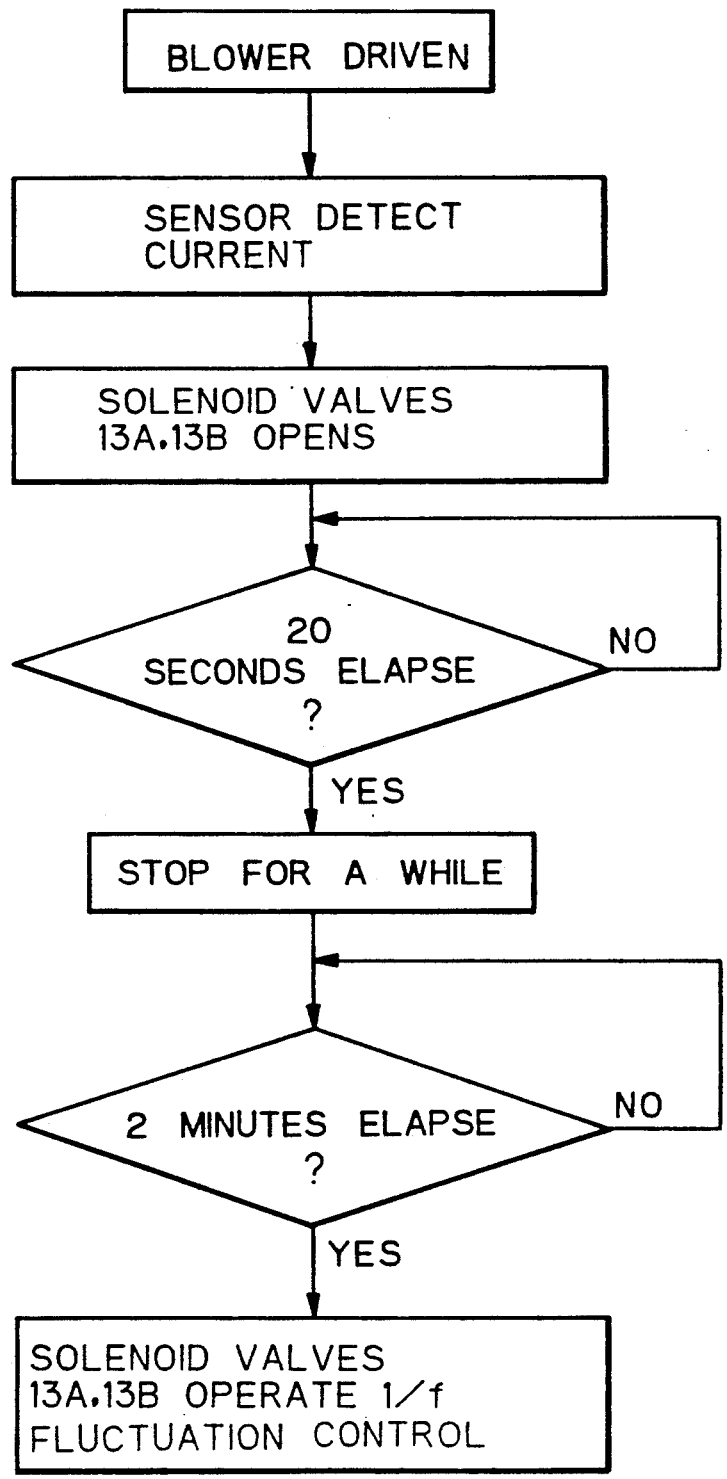
FIG. 13 is a flow chart of the control of a valve control circuit in the case of use of a fragrance.

FIG. 13 is a flow chart of the operation of the valve control circuit in the case of use of a fragrance. When the blower starts to be operated, the current sensor detects the current and the solenoid valves 12A and 12B are opened for a predetermined time, for example 20 seconds, to diffuse the fragrance into the conditioned air. After the elapse of the predetermined time, the solenoid valves are closed to stop the diffusion of the fragrance. After another predetermined time, for example, 2 minutes, the solenoid valves 12A and 12B are opened and closed intermittently by 1/f fluctuation control, for example, as explained in the first embodiment of the invention.

According to this embodiment of the invention, the inlet pipe 31 and the outlet pipe 32 can be easily attached without major modification of the air-conditioning system, so the fragrance supplying apparatus can be installed in various existing air-conditioner systems as a later option. Further, since the deodorant is discharged for a short period immediately after the start of the air-conditioning, the deodorant is not wasted.

Note that in addition to using a current sensor to detect the start of the blower, use may be made of an air pressure sensor or an air flow sensor installed immediately after the blower. The air pressure sensor may be a semiconductor sensor, a switch, etc. which senses the movement of a receiving plate in the air stream. The air flow sensor may be a sensor which detects the difference between the outputs of a temperature sensor subjected to the air flow and one not subjected to it.

Figure 14:
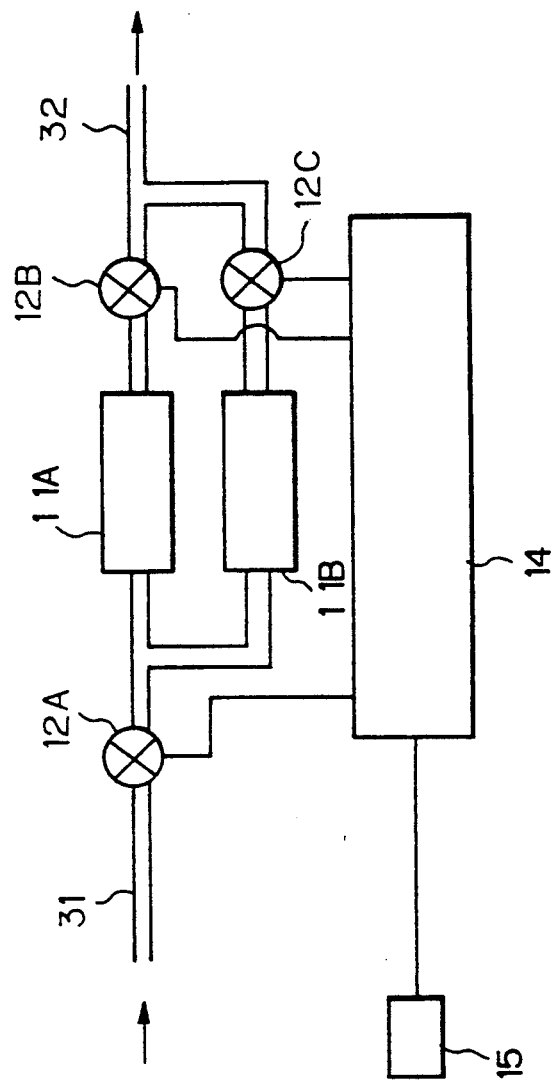
FIG. 14 is a block diagram of a fragrance supplying apparatus according to a modification of the second embodiment of the invention.
Figure 15:
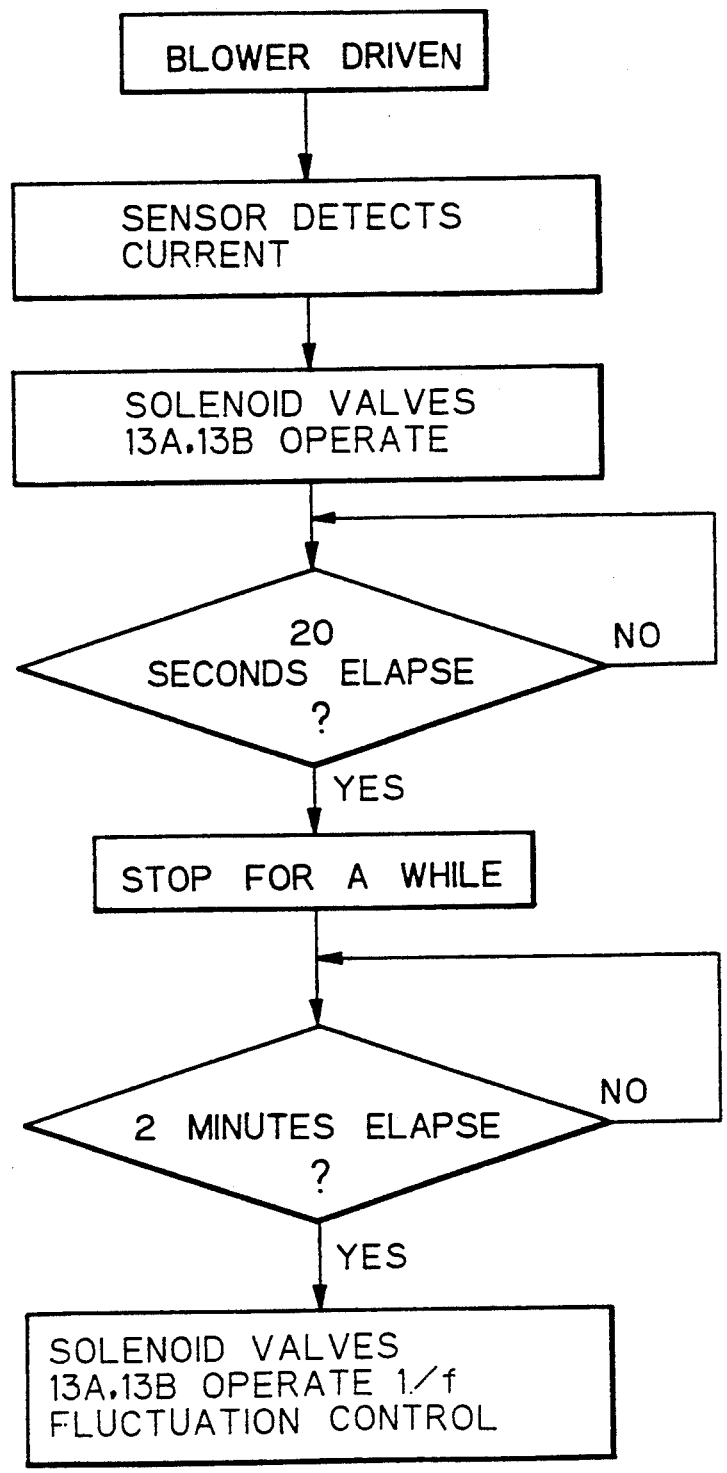
FIG. 15 is a flow chart of the control in the case of the modification of FIG. 14.

FIG. 14 shows a modification of the second embodiment of the present invention, and FIG. 15 is a flow chart of the control in this modification. In this modification, two types of cassettes are provided: a cassette 11A containing a deodorant and a cassette 11B containing a fragrance. A solenoid valve 13A is provided before the cassettes 11A and 11B and solenoid valves 13B and 13C are provided after them. The solenoid valves 13A and 13B are opened to supply the deodorant into the conditioned air for the 20 seconds after the startup of the blower, as shown in FIG. 15. After the 20 seconds elapse, the solenoid valves 13A and 13B are closed. Two minutes after that, the solenoid valves 13A and 13C are opened and closed intermittently by 1/f fluctuation control to supply the fragrance of the cassette 11B into the conditioned air.

As set forth above, according to this embodiment of the fragrance supplying apparatus of the present invention, the fragrance supplying apparatus can be easily installed in various kinds of air-conditioning systems as a later option and waste of the fragrance can be prevented.

Figure 16:
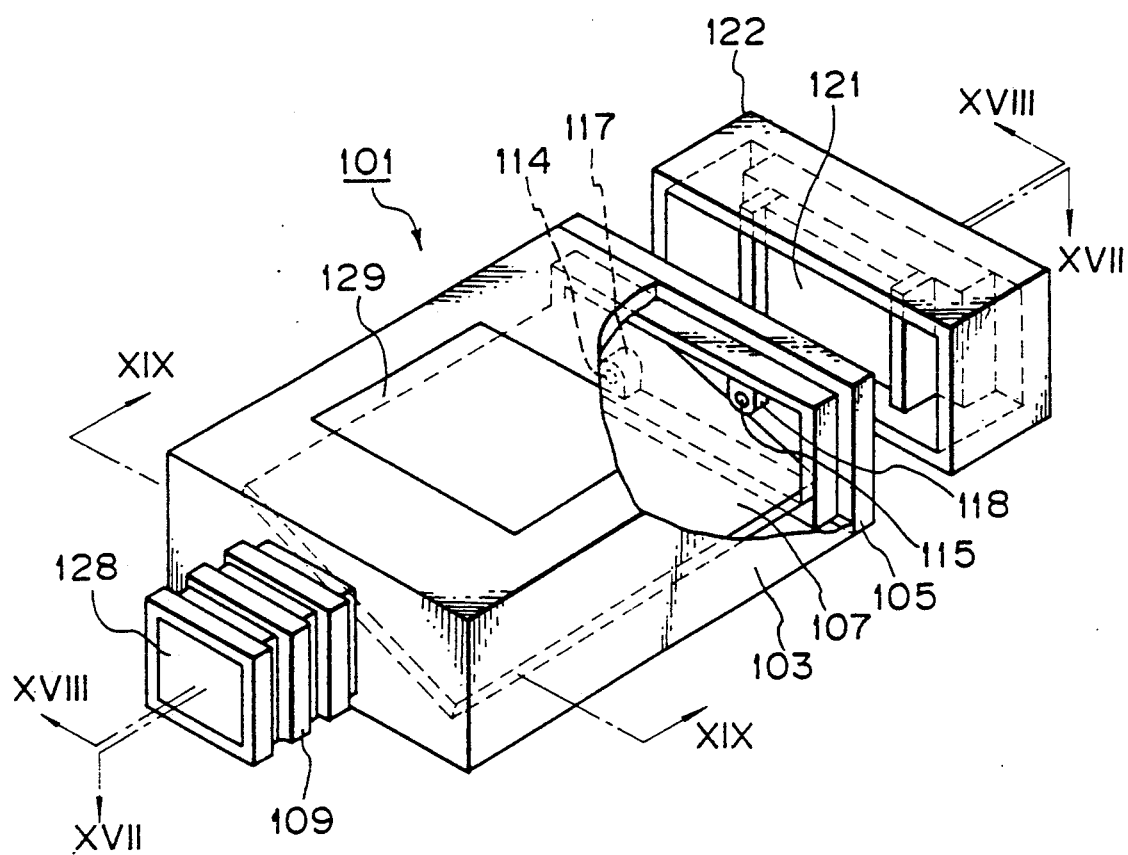
FIG. 16 is an exploded partially sectional view of a fragrance cassette of the present invention.
Figure 17:
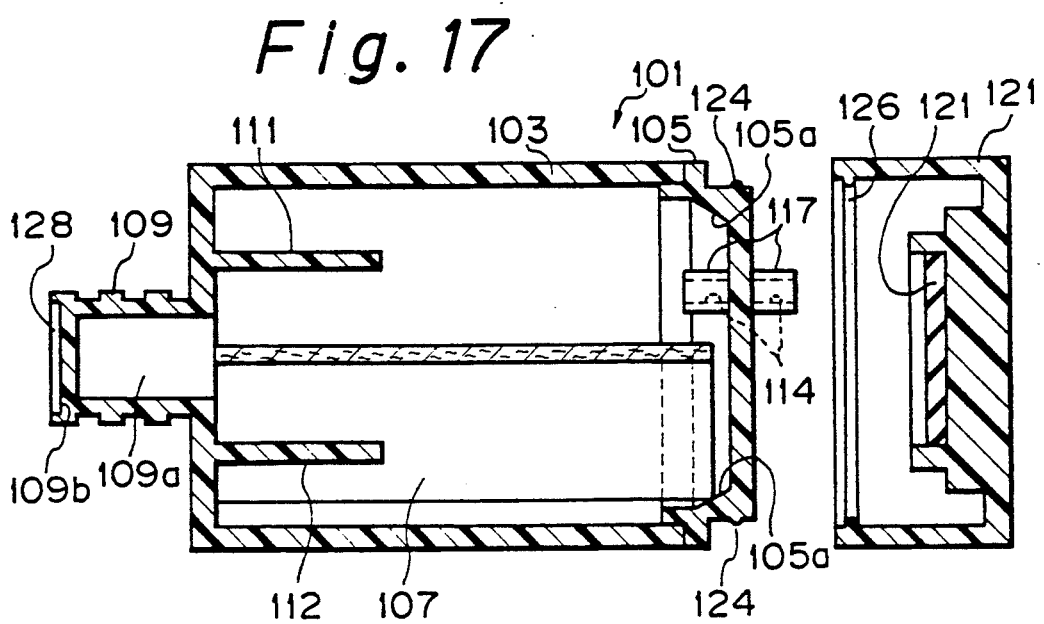
FIG. 17 to FIG. 19 are sectional views taken along lines 17—17, 18—18, and 19—19 of FIG. 7 and illustrate the internal structure of the fragrance cassette of FIG. 16.
Figure 18:
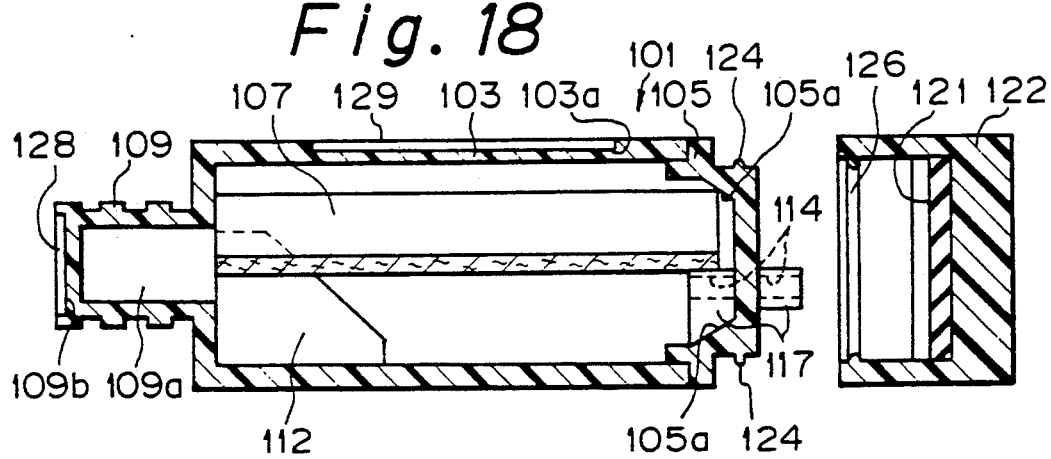
Figure 19:
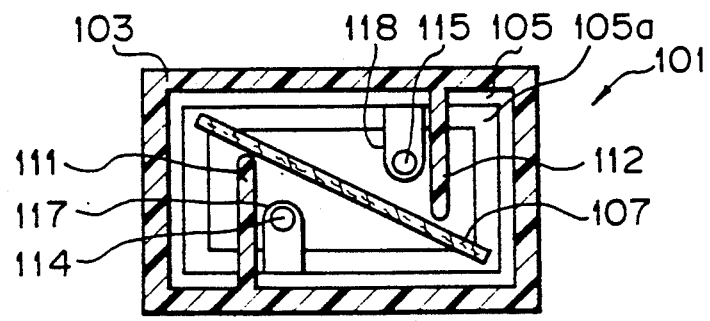

FIG. 16 is a partially cutaway perspective view of a fragrance cassette of the present invention. FIGS. 17 to 19 are sectional views of the internal construction of the same taken along lines XVII—XVII, XVIII—XVIII, and XIX—XIX, respectively, of FIG. 16.

In FIG. 16, the fragrance cassette 101 includes a cassette body 103, formed from a chemically resistant, that is, fragrance resistant, plastic material such as POM, PBT, and PET into a hollow box with One end face open, and a lid body 105, also formed from a chemically resistant plastic material and closing the opening of the cassette body 103.

The fragrance cassette 101 holds within it filter paper 107 impregnated with a fragrance and/or a deodorant. After the filter paper 107 is inserted into the cassette body 103, the lid body 105 is fitted over the opening portion of the cassette body 103 and welded there by ultrasonic waves.

The outer wall of the end face of the cassette body 103 opposite to the lid body 105 is provided with a knob 109 having a hollow portion 109a communicating with the interior of the cassette body 103. At the inner side walls of the knob 109 are provided a pair of lock plates 111 and 121 for keeping the filter paper 107 in the cassette at an angle.

The lid body 105 is also provided with a pair of pipes 117 and 118 having through holes 114 and 115 for supplying and discharging air in the cassette body 103. These are formed sandwiching the filter paper 107 between them. At an inner wall of the lid body 105 is provided a sloping surface 105a that is formed to abut against one corner of the filter paper 107 and fix the filter paper 107 to an inner side wall of the knob 109 of the cassette body 103.

At a peripheral edge of the outer wall of the lid body 105 is provided a projecting edge 124 for attaching a stopper 122 that has a gasket 121 preventing the fragrance component from escaping outside when the casette 101 is not used. The projecting edge 124 fits over the end of the pipes 117 and 118 to engage a projecting edge 126 formed in the stopper 122.

The end surface of the knob 109 and the upper surface of the cassette body 3 are respectively provided with depressed parts 109b and 103a for holding seals 128 and 129 indicating the kind of fragrance or deodorant in the cassette to provide the user with information on its contents.

Since the cassette 101 is provided with a pair of pipes 117 and 118 having the holes 114 and 115 for supplying and discharging air in the cassette, when supplying air from one pipe 117 (or 118) into the cassette, air including a fragrance from the filter paper 107 in the cassette is discharged from the other pipe 118 or 117). The amount of discharge of the fragrance is determined by the amount and frequency of supplying air into the cassette. By controlling the supply of air into the cassette, the fragrance may be diffused at a desired rate.

In the cassette 101, the pipes 117 and 118 sandwich the filter paper 107 between them, but in the cassette 101, air passages are formed by the lid body 105 between the upper and lower end edges of the filter paper 107 and the vessel body 103 and between the side end edges of the filter paper 107 and the lid body 105. An air passage is formed by the hollow part 109a of the knob 109 so that air supplied from one pipe 117 (or 118) is discharged from the other pipe 118 (or 117) through the upper, lower, left, and right end edges of the filter paper 107. Therefore, when supplying air from one pipe 117 (or 118), all of the fragrance evaporating from the front and back surface may be introduced and discharged into the other pipe 118 (or 117). Accordingly, there is no part of the fragrance component evaporating from the filter paper 107 which remains and so the fragrance impregnated at one portion will not be greater than that at another portion. That is, the fragrance impregnated in the filter paper 107 evaporates from the front and back surface at a constant rate and the fragrance diffuses more stably.

In the cassette 101, the knob 109 enables the cassette to be easily moved and installed. In the case of using it installed in a fragrance supplying apparatus, the cassette 101 allows for easy attachment.

The seals 128 and 129 showing the kind of the fragrance accommodated in the cassette are difficult to peel off, so identification of the fragrance is ensured. Also, the stopper 122 having the gasket 121 at the projecting edge 124 of the outer wall of the lid body 105 prevents the fragrance from escaping outside when not using the cassette 101.

Next, the mounting of a cassette 101 in a fragrance supplying apparatus will be discussed.

Figure 20:
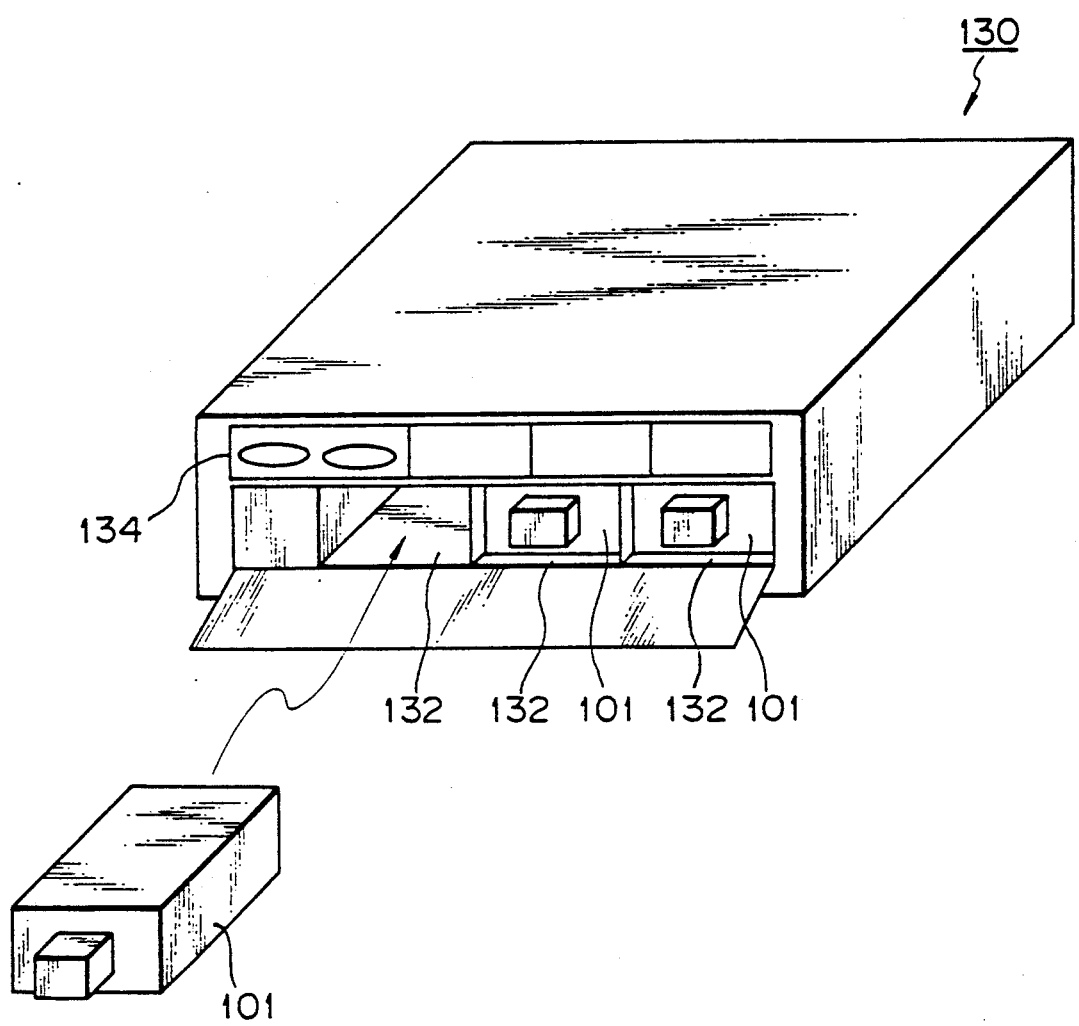
FIG. 20 is a view of the outside of an embodiment of the fragrance supplying apparatus.

As shown in FIG. 20, a fragrance supplying apparatus 130 is provided at the front with three bays 132 for holding cassettes 101. The cassettes 101 may be fitted in them by ripping the knobs 109 and pushing the cassettes 101 into the bays 132. When not inserting a cassette 101 into a bay 132, the air passage in the bay is blocked.

The fragrance supplying apparatus supplies air to the three cassettes 101 in the bays 132, blows the desired fragrance from an outlets of the air-conditioner, and thus removes or masks the odors in the vehicle cabin. A the front surface of the apparatus, there is provided an operating panel 134 including switches for setting the fragrance used and the amount of the fragrance blown outside and display lamps that display the operating states.

Figure 21:
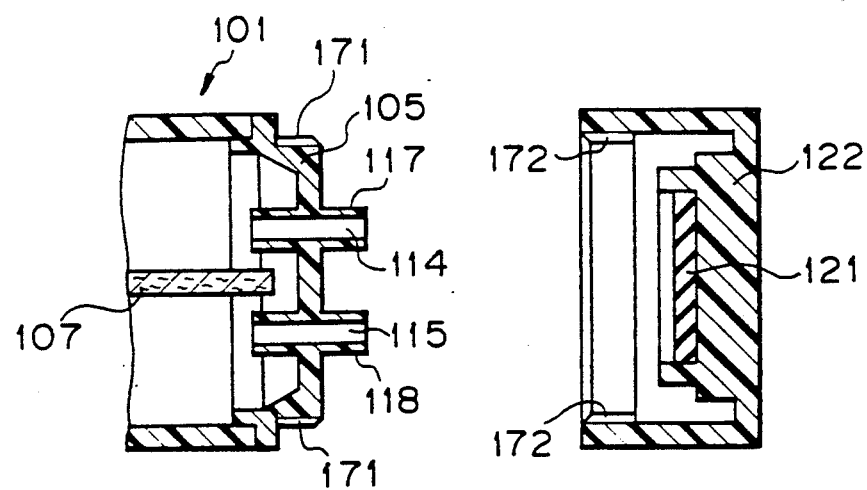
FIG. 21 is a sectional view of a modification of the fragrance cassette.

While an example of the fragrance cassette 101 was discussed above, the fragrance cassette 101 is not limited to the above example. Various modifications are possible within the scope of the claims. For example, in the above example, seals were applied to indicate the type of the fragrance in the cassettes, but the types of the fragrances may be directly indicated on the cassettes when molding them, which would further improve the design of the cassettes. Also, in the above example, the projecting edge 124 was formed at the outside wall of the lid body 105 and engaged with the projecting edge 126 formed on the stopper 122. By attaching gaskets 121 to the outside ends of the pipes 117 and 118, the fragrance component was prevented from escaping outside when the cassettes were not being used. As shown in FIG. 21, however, the cassette 101 and the stopper 122 may be formed in a cylindrical shape, the lid body 105 and the stopper 122 provided with threaded portions 171 and 172, and the threaded portion 171 and 172 engaged when a cassette is not used so as to make the gasket 121 abut against the outside ends of the pipes 117 and 118, thereby more reliably preventing the fragrance component from escaping. Note that in FIG. 22, parts corresponding to those in the previous figures are given the same reference numerals and explanations of the same are omitted.

As explained above, in the fragrance cassette, air is supplied from one hole so that air including the fragrance component is discharged from the other hole to diffuse the fragrance component in a more stable manner. Also, the outside wall of the cassette is provided with a knob enabling easier mounting on other equipment, such as air-conditioners.

We claim:

1. An fragrance supplying apparatus for a vehicle for supplying an interior of an air-conditioning duct of the vehicle with a fragrance or deodorant so that the fragrance or deodorant is carried by a flow of air from a blower of the air-conditioning system into the cabin of the vehicle, the fragrance supplying apparatus comprising:
   a fragrance supplying means having control valves for controlling the supply of the fragrance or deodorant into the air-conditioning duct;
   a random number producing means for producing random numbers; and
   a control means for controlling the control valves of the fragrance supplying means based on the random numbers to set varying patterns of supply and cessation of the fragrance or deodorant.

2. A fragrance supplying apparatus for a vehicle as set forth in claim 1, wherein the random number producing means produces random numbers representing a time and interval for supplying the fragrance or deodorant.

3. A fragrance supplying apparatus for a vehicle as set forth in claim 1, wherein the random number producing means produces random numbers representing a time and interval for supplying the fragrance or deodorant, a power spectrum and frequency of the supply of fragrance or deodorant being inversely proportional.

4. A fragrance supplying apparatus for a vehicle as set forth in claim 1, wherein the fragrance supplying means is provided with a startup detector detecting startup of the blower and supplies the fragrance or deodorant to the air-conditioning duct by the control valves when the startup of the blower is detected.

5. A fragrance supplying apparatus for a vehicle as set forth in claim 4, wherein the startup detector is a current sensor detecting current flowing in a feeder connected to a motor of the air-conditioning system to supply power for the blower.

6. A fragrance supplying apparatus for a vehicle as set forth in claim 1, wherein the fragrance supplying means opens the control valves for a predetermined time after detecting the startup of the blower to mix the fragrance or deodorant in the air flow in the duct, closes the control valves for a while when the predetermined time elapses, and then intermittently Opens and closes the control valves by the control means when another predetermined time elapses.

7. A fragrance supplying apparatus for a vehicle as set forth in claim 1, wherein the fragrance supplying means includes a cassette holding a deodorant and a cassette holding a fragrance, the deodorant or fragrance being carried in the air flow from the duct for a predetermined time after the startup of the blower and then not being carried for a while after the predetermined time elapses and further the fragrance or deodorant being carried intermittently in the air flow from the duct by the control means when another time elapses.

8. A fragrance supplying apparatus for a vehicle for supplying an air-conditioner with a fragrance or deodorant so that the fragrance or deodorant is carried by a flow of air from the air-conditioner into the cabin of the vehicle, the air-conditioner having an inlet pipe downstream of a blower for receiving air from the blower and an outlet pipe for introducing air into air outlets, the fragrance supplying apparatus comprising:
   at least one fragrance supplying means for supplying the air-conditioning system with a fragrance or deodorant, the means comprising:
      a first connecting means for connecting to the outlet pipe;
      a second connecting means for connecting to the inlet pipe;
      control valves operable to form air passages between the downstream side of the blower and the outlets via the first connecting means, fragrance cassette, and second connecting means;
      a random number producing means for producing random numbers; and
      a control means for controlling the control valves of the fragrance supplying means based on the random numbers to set varying patterns of supply and cessation of the fragrance or deodorant.

9. A fragrance supplying apparatus for a vehicle as set forth in claim 8, wherein the random number producing means produces random numbers representing a time and interval for supplying the fragrance or deodorant.

10. A fragrance supplying apparatus for a vehicle as set forth in claim 8, wherein the random number producing means produces random numbers representing a time and interval for supplying the fragrance or deodorant, a power spectrum and frequency of the supply of fragrance or deodorant being inversely proportional.

11. A fragrance supplying apparatus for a vehicle as set forth in claim 8, wherein the fragrance supplying means is provided with a startup detector detecting startup of the blower and supplies the fragrance or deodorant to the air-conditioning duct by the control valves when the startup of the blower is detected.

12. A fragrance supplying apparatus for a vehicle as set forth in claim 11, wherein the startup detector is a current sensor detecting current flowing in a feeder connected to a motor of the air-conditioning system to supply power for the blower.

13. A fragrance supplying apparatus for a vehicle as set forth in claim 1, wherein the fragrance supplying means opens the control valves for a predetermined time after detecting the startup of the blower to mix the fragrance or deodrant in the air flow in the duct, closes the control valves for a while when the predetermined time elapses, and then intermittently opens and closes the control valves by the control means when another predetermined time elapses.

14. A fragrance supplying apparatus for a vehicle as set forth in claim 8, wherein the fragrance supplying means includes a cassette holding a deodorant and a cassette holding a fragrance, the deodorant or fragrance being carried in the air flow from the air-conditioner for a predetermined time after the startup of the blower and then not being carried for a while after the predetermined time elapses and further the fragrance or deodorant being carried intermittently in the air flow from the air-conditioner by the control means when another time elapses.

15. A fragrance supplying apparatus for a vehicle for supplying a fragrance or deodorant to a flow of air produced by a blower, the fragrance supplying apparatus comprising:
   a fragrance supplying means for supplying a fragrance or deodorant and introducing it into the flow of air;
   a random number producing means for producing random numbers; and
   a control means for controlling the fragrance supplying means, including a control circuit for setting on and off times for introduction of the fragrance or deodorant based on the random numbers to set varying patterns of supply and cessation of the fragrance or deodorant.

16. A fragrance supplying apparatus for a vehicle as set forth in claim 15, wherein the random number producing means produces random numbers representing a time and interval for supplying the fragrance or deodorant.

17. A fragrance supplying apparatus for a vehicle as set forth in claim 15, wherein the random number producing means produces random numbers representing a time and interval for supplying the fragrance or deodorant, a power spectrum and frequency of the supply of fragrance or deodorant being inversely proportional.

18. A fragrance supplying apparatus for a vehicle as set forth in claim 15, wherein the fragrance supplying means is provided with a startup detector detecting startup of the blower and supplies the fragrance or deodorant to the air-conditioning duct by the control valves when the startup of the blower is detected.

19. A fragrance supplying apparatus for a vehicle as set forth in claim 18, wherein the startup detector is a current sensor detecting current flowing in a feeder connected to a motor of the air-conditioning system to supply power for the blower.

20. A fragrance supplying apparatus for a vehicle as set forth in claim 18, wherein the fragrance supplying means opens the control valves for a predetermined time after detecting the startup of the blower to mix the fragrance or deodorant in the air flow in the air-conditioning duct, closes the control valves for a while when the predetermined time elapses, and then intermittently opens and closes the control valves by the control means when another predetermined time elapses.

21. A fragrance supplying apparatus for a vehicle as set forth in claim 15, wherein the fragrance supplying means includes a cassette holding a deodorant and a cassette holding a fragrance, the deodorant or fragrance being carried in the air flow from the air-conditioning duct for a predetermined time after the startup of the blower and then not being carried for a while after the predetermined time elapses and further the fragrance or deodorant being carried intermittently in the air flow from the air-conditioning duct by the control means when another time elapses.

22. A fragrance supplying apparatus for a vehicle for supplying an interior of an air-conditioning duct of the vehicle with a fragrance or deodorant so that the fragrance or deodorant is carried by a flow of air from a blower of the air-conditioning system into the cabin of the vehicle, the air fragrance apparatus comprising:
- a fragrance supplying means having control valves for controlling the supply of the fragrance or deodorant into the air-conditioning duct and
- means for randomly controlling the control valves to set varying patterns of supply and cessation of the fragrance or deodorant.

23. A fragrance supplying apparatus for a vehicle as set forth in claim 22, wherein the fragrance supplying means is provided with a startup detector detecting startup of the blower and supplies the fragrance or deodorant to the air-conditioning duct by the control valves when the startup of the blower is detected.

24. A fragrance supplying apparatus for a vehicle as set forth in claim 22, wherein the startup detector is a current sensor detecting current flowing in a feeder connected to a motor of the air-conditioning system to supply power for the blower.

25. A fragrance supplying apparatus for a vehicle as set forth in claim 23, wherein the fragrance supplying means opens the control valves for a predetermined time after detecting the startup of the blower to mix the fragrance or deodorant in the air flow in the air-conditioning duct, closes the control valves for a while when the predetermined time elapses, and then intermittently opens and closes the control valves by the control means when another predetermined time elapses.

26. A fragrance supplying apparatus for a vehicle as set forth in claim 22, wherein the fragrance supplying means includes a cassette holding a deodorant and a cassette holding a fragrance, the deodorant or fragrance being carried in the air flow from the air-conditioning duct for a predetermined time after the startup of the blower and then not being carried for a while after the predetermined time elapses and further the fragrance or deodorant being carried intermittently in the air flow from the air-conditioning duct by the control means when another time elapses.

27. A fragrance supplying apparatus for a vehicle for supplying an interior of an air-conditioning duct of the vehicle with a fragrance or deodorant so that the fragrance or deodorant is carried by a flow of air from a blower of the air-conditioning system into the cabin of the vehicle, the air fragrance apparatus comprising:
- a fragrance supplying means having control valves for controlling the supply of the fragrance or deodorant into the air-conditioning duct,
- a startup detector detecting startup of the blower, the startup detector being a current sensor detecting current flowing in a feeder connected to a motor of the air-conditioning system to supply power for the blower, and
- means for controlling the control valves to send a deodorant in the air flow for a predetermined time after startup of the blower and not send it for a while when the predetermined time elapses and further to send intermittently a fragrance or deodorant in the air flow when another predetermined time elapses.

28. A fragrance supplying apparatus for a vehicle for supplying an interior of an air-conditioning duct of the vehicle with a fragrance or deodorant so that the fragrance or deodorant is carried by a flow of air from a blower of the air-conditioning system into the cabin of the vehicle, the air fragrance apparatus comprising:
- a fragrance supplying means having control valves for controlling the supply of the fragrance or deodorant into the air-conditioning duct,
- a startup detector detecting startup of the blower, the startup detector being a current sensor detecting current flowing in a feeder connected to a motor of the air-conditioning system to supply power for the blower, and
- means for controlling the control valves to send a fragrance or deodorant in the air flow for a predetermined time after startup of the blower.

29. A fragrance supplying apparatus for a vehicle as set forth in claim 1, wherein the fragrance supplying means has a plurality of fragrance or deodorant cassettes and the control valves are provided at outlets corresponding to the fragrance or deodorant cassettes.

30. A fragrance supplying apparatus for a vehicle as set forth in claim 29, wherein the fragrance supplying means has a switching means for switching and selecting the fragrance or deodorant cassettes.

* * * * *